United States Patent [19]

Arrick

[11] Patent Number: 4,563,345

[45] Date of Patent: Jan. 7, 1986

[54] CHEWING GUM

[76] Inventor: Robert A. Arrick, 87 Indian Ave., Portsmouth, R.I. 02871

[21] Appl. No.: 572,988

[22] Filed: Jan. 23, 1984

[51] Int. Cl.$^4$ .................... A61K 9/68; A61K 7/18
[52] U.S. Cl. .................................. 424/48; 426/3; 424/52; 424/151
[58] Field of Search .................... 424/48, 52, 151; 426/3-6

[56] References Cited

U.S. PATENT DOCUMENTS

| | | | |
|---|---|---|---|
| 810,210 | 1/1906 | Laws | 426/5 |
| 2,627,493 | 2/1953 | Merckel et al. | 167/93 |
| 2,700,012 | 1/1955 | Merckel et al. | 167/93 |
| 2,798,023 | 7/1957 | Berger | 424/280 |
| 3,075,884 | 1/1963 | Bilotti et al. | 167/82 |
| 3,337,412 | 8/1967 | Elbreder | 424/151 |
| 3,894,154 | 6/1975 | Graff et al. | 426/5 |
| 4,156,740 | 5/1979 | Glass et al. | 426/3 |
| 4,228,150 | 10/1980 | Robyt et al. | 424/48 |
| 4,233,288 | 11/1980 | Cornell | 424/48 |
| 4,238,475 | 12/1980 | Witzel et al. | 424/48 |
| 4,265,877 | 5/1981 | Tenta | 424/48 |
| 4,267,167 | 5/1981 | Weitzman et al. | 424/151 |
| 4,284,650 | 8/1981 | Goupil | 426/5 |
| 4,301,178 | 11/1981 | Witzel et al. | 426/5 |
| 4,316,915 | 2/1982 | Friello et al. | 426/5 |

FOREIGN PATENT DOCUMENTS

| | | | |
|---|---|---|---|
| 949555 | 9/1949 | France | 426/3 |
| 988472 | 8/1951 | France | 426/3 |

OTHER PUBLICATIONS

J.A.S.P.D., pp. 17-21, 36-45, Jan., Feb. 1975, Everything You Always Wanted to Know About Fluoride Therapy.

Englander et al., J.A.D.A. 78: 783-787, Apr. 1969, Residual Anticaries Effect of Repeated Topical Sodium Fluoride Applications by Mouthpieces.

Englander et al., J.A.D.A. 75: 638-644, Sep. 1967, Clinical Anticaries Effect of Repeated Topical Sodium Fluoride Applications by Mouthpieces.

Carter, Midwest Dental J. 43: 17-18 (1967), The Effect of a Daily Neutral Fluoride Gel on Active Caries Patients.

Law, J.A.D.A. 73: 855-837, Oct. 1966, Peace Corps Dental Program.

*Primary Examiner*—Shep K. Rose

[57] ABSTRACT

A piece of chewing gum having a first phase including a chewable material, and a second phase including a tooth decay inhibiting amount of an effective fluorine salt, the first phase enclosing the second phase and not being admixed therewith.

10 Claims, 1 Drawing Figure

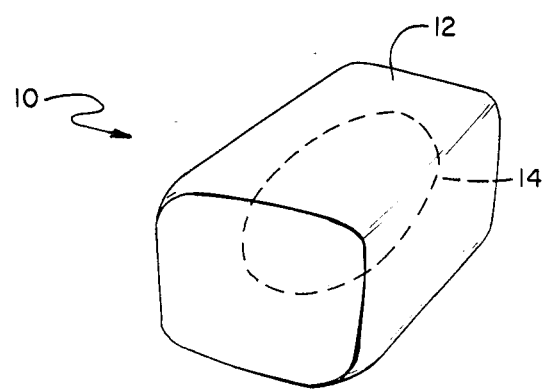

CHEWING GUM

BACKGROUND OF THE INVENTION

This invention relates to tooth decay preventing chewing gum.

A number of patents, hereby incorporated by reference, describe decay-preventive chewing gum admixed with fluorine-containing salts: Robyt et al. U.S. Pat. No. 4,228,150; Terta et al. U.S. Pat. No. 4,265,877; Goupil U.S. Pat. No. 4,284,650; Cornell U.S. Pat. No. 4,233,288; Bilotti et al, U.S. Pat. No. 3,075,884; Merckel et al. U.S. Pat. No. 2,627,493; and Merckel et al. U.S. Pat. No. 2,700,012.

SUMMARY OF THE INVENTION

I have discovered that it is advantageous to provide a fluorine salt in a separate phase enclosed in the chewable material, rather than admixing the fluorine salt with the chewable material.

Accordingly, the present invention features, in general, a piece of chewing gum composed of a first phase including a chewable material, and a second phase including a tooth decay inhibiting amount of an effective fluorine salt, the first phase enclosing the second phase and not being admixed therewith.

In preferred embodiments, the second phase is, at room temperature, a liquid which has a viscosity sufficiently high to cause at least a portion of the second phase fluorine salt to adhere to tooth enamel; preferably the viscosity of the second phase at room temperature is between 10 and 120 times as viscous as water, as defined by a test in which a drop is allowed to travel 15 mm down a polished surface inclined at 45°. A drop of water travels this distance in slightly less than one second, while the second phase of the invention preferably travels this distance in between 10 and 120 seconds, most preferably in 60 seconds.

In other preferred embodiments, the second phase includes a non-toxic, pharmaceutically acceptable carrier substance, e.g., distilled water, and a thickening agent, e.g., sodium carboxymethycellulose, which imparts the desired viscosity.

In other preferred embodiments, the fluorine salt is sodium fluoride, and the second phase includes a flavoring agent, e.g., aspartame and a preservative, e.g. methylparaben.

A preferred second phase has a volume of 0.25-0.75 ml and the following general formulation:
between 0.3 and 0.5 g fluorine salt,
between 50 and 250 g of a 5-25% solution of a thickening agent,
between 50 and 150 mg of a 0.5%-0.2% solution of a preservative,
an effective amount of a flavoring agent, and
water to make 1 liter of solution.

The chewing gum of the invention, because of its unique two-phase structure, delivers fluoride ions to the user in a form which is beneficially both ingested and applied topically to tooth enamel. Furthermore, where the liquid second phase is of high viscosity, some of the fluoride ions adhere to tooth enamel, lengthening the tooth exposure time for each fluoride ion, thus providing greater per-molecule efficiency. This last advantage is of particular importance because of the desirability of using small doses of fluoride, fluoride being toxic in large doses.

Other features and advantages of the invention will be apparent from the following description of the preferred embodiment, and from the claims.

DESCRIPTION OF THE PREFERRED EMBODIMENT

We first briefly describe the drawing.

The FIGURE is a perspective view, partially broken away, of a piece of chewing gum of the invention.

STRUCTURE

Referring to the FIGURE, piece of gum 10 is in the shape of a rectangular box with rounded edges. The piece is made up of a first phase 12 enclosing and not admixed with second phase 14.

First phase 12 is composed of conventional chewing gum material containing the plant resin chicle.

Second phase 14 is 0.50 ml of the following solution:
Sodium Fluoride USP: 0.402 gm
Sodium Carboxymethycellulose USP (10%-20%): 100-200 gm
Methylparaben (0.1%): 100 mg
Oil of Cinnamon: 4 mg
Aspartame (2%): 20 gm
Distilled water to make 1000 ml of solution.

Second phase 14 contains approximately 0.075 mg of fluoride ion.

Manufacture

Piece of gum 10 is made by a conventional method used in the manufacture of liquid-center chewing gum. Such methods have long been known, one being described, e.g., in Laws U.S. Pat. No. 810,210, hereby incorporated by reference.

Use

The piece of gum is chewed by a person in need of fluoride, at a rate, say one or two pieces per day, effective to provide the amount of fluoride ion desired.

The viscous, fluoride-containing second phase is released into the mouth immediately upon sufficient chewing to rupture the first phase. A portion of the viscous liquid adheres to the teeth, providing topical protection, while the remainder of the fluoride is ingested for additional protection.

Other Embodiments

Other embodiments are within the following claims. For example, a wide variety of first and second phase formulations can be used; e.g., many different types of flavorings, thickening agents, and preservatives, as well as various fluoride salts, can be employed.

The amount of fluoride salt in an individual piece of gum can vary, depending on various parameters, e.g. the number of pieces chewed each day, the age of the user, and whether the user regularly drinks fluoridated water or uses fluoridated toothpaste. A greater amount of fluoride might be present in chewing gum, for example, which is used in third world countries where no fluoride of any type is available.

I claim:

1. A piece of liquid center chewing gum comprising a first phase comprising chewing gum, and a high viscosity viscous second phase comprising a tooth decay inhibiting amount of between 0.3 and 0.5 g. of sodium fluoride USP, toxic in large doses, as an effective fluorine salt and between 50 and 250 g. of a 5-25% solution of a thickening agent adapted to impart sufficiently high viscosity to adhere some of the fluoride ions to tooth enamel, said first phase enclosing said second phase and not being admixed therewith, said high-viscosity viscous, fluoride-containing second phase being released into the mouth immediately upon sufficient chewing to rupture said first phase whereby a portion of said viscous second phase adheres to the teeth, providing topical protection, while the remainder of the fluoride is ingested, in smaller than toxic doses, for additional protection.

2. The piece of claim 1 wherein said second phase is a liquid at room temperature.

3. The piece of claim 2 wherein said liquid second phase has a viscosity at room temperature sufficiently high to cause at least a portion of said second phase to adhere to tooth enamel.

4. The piece of claim 3 wherein said liquid second phase has a viscosity at room temperature between 10 and 120 times that of water, as defined by the length of time taken to travel down an inclined surface.

5. The piece of claim 3 wherein said second phase further comprises a non-toxic, pharmaceutically acceptable liquid carrier substance, and a non-toxic, pharmaceutically acceptable thickening agent in an amount sufficient to impart said sufficiently high viscosity.

6. The piece of claim 5 wherein said thickening agent comprises sodium carboxymethycellulose.

7. The piece of claim 1 wherein said second phase further comprises an effective amount of a flavoring agent.

8. The piece of claim 1 wherein said second phase further comprises an effective amount of a non-toxic preservative.

9. The piece of claim 5 wherein said second phase comprises between 0.25 and 0.75 ml of a solution comprising between 0.3 and 0.5 g fluorine salt, between 50 and 250 g of a 5–25% solution of a thickening agent, between 50 and 150 mg of a 0.5%–0.2% solution of a perservative, an effective amount of a flavoring agent, and water to make 1 liter of solution.

10. The piece of claim 9 wherein said fluorine salt comprises sodium fluoride, said thickening agent comprises sodium carboxymethycellulose, said preservative comprises methylparaben, and said flavoring agent comprises aspartame.

* * * * *